(12) United States Patent
Halstrom

(10) Patent No.: US 8,931,486 B2
(45) Date of Patent: Jan. 13, 2015

(54) INTRA-ORAL APPLIANCE FOR TREATMENT OF SLEEP DISORDERS

(75) Inventor: Leonard Wayne Halstrom, Lion's Bay (CA)

(73) Assignee: Donald Lorne Halstrom, Surrey (CA)

( * ) Notice: Subject to any disclaimer, the term of this patent is extended or adjusted under 35 U.S.C. 154(b) by 917 days.

(21) Appl. No.: 11/424,221

(22) Filed: Jun. 14, 2006

(65) Prior Publication Data
US 2008/0000483 A1    Jan. 3, 2008

(51) Int. Cl.
*A61F 5/56*    (2006.01)

(52) U.S. Cl.
CPC ..................................... *A61F 5/566* (2013.01)
USPC .......................... 128/848; 128/859; 128/861

(58) Field of Classification Search
USPC .......................................... 128/848, 859, 861
See application file for complete search history.

(56) References Cited

U.S. PATENT DOCUMENTS

| | | |
|---|---|---|
| 1,146,264 A | 7/1915 | Kelly |
| 4,416,626 A | 11/1983 | Bellavia |
| 4,433,956 A | 2/1984 | Witzig |
| 4,505,672 A | 3/1985 | Kurz |
| 4,618,324 A | 10/1986 | Nord |
| 4,619,609 A | 10/1986 | Clark |
| 4,715,368 A | 12/1987 | George |
| 4,901,737 A | 2/1990 | Toone |
| 4,969,822 A | 11/1990 | Summer |
| 5,002,485 A | 3/1991 | Aagesen |
| 5,003,994 A | 4/1991 | Cook |
| 5,066,226 A | 11/1991 | Summer |
| 5,092,346 A | 3/1992 | Hays et al. |
| 5,103,838 A | 4/1992 | Yousif |
| 5,117,816 A | 6/1992 | Shapiro et al. |

(Continued)

FOREIGN PATENT DOCUMENTS

| | | |
|---|---|---|
| DE | 2 320 501 | 4/1973 |
| EP | 0 182 387 | 5/1986 |

(Continued)

OTHER PUBLICATIONS

Dr. Alan Lowe, "Dental Appliances for the Treatment of Snoring and/or Obstructive Sleep Apnea", Feb. 21, 1991.

(Continued)

*Primary Examiner* — Patricia Bianco
*Assistant Examiner* — Keri J Nelson
(74) *Attorney, Agent, or Firm* — Oyen Wiggs Green & Mutala LLP

(57) ABSTRACT

An intra-oral dental appliance for treatment of sleep disorders including snoring, sleep apnea and nocturnal bruxism. The appliance includes an upper member conforming to the patient's maxillary dentition; a lower member conforming to the patient's mandibular dentition; and a connecting assembly for adjustably coupling the upper and lower members together. The connecting assembly includes a first element mounted on the upper member, the first element having a cavity therein; a second element mounted on the lower member; and a connector having a first end captured within the cavity and a second end adjustably connectable to the second element. The connecting assembly maintains the lower member in a protruded position relative to the upper member to maintain the patency of the user's pharnygeal airway while permitting anterior and lateral movement of the lower member relative to the upper member in the protruded position.

34 Claims, 4 Drawing Sheets

(56) References Cited

U.S. PATENT DOCUMENTS

| | | |
|---|---|---|
| 5,195,890 A | 3/1993 | Johansson et al. |
| 5,203,324 A | 4/1993 | Kinkade |
| 5,277,202 A | 1/1994 | Hays |
| 5,313,960 A | 5/1994 | Tomasi |
| 5,352,116 A | 10/1994 | West |
| 5,365,945 A | 11/1994 | Halstrom |
| 5,409,017 A | 4/1995 | Lowe |
| 5,427,117 A | 6/1995 | Thornton |
| 5,499,633 A | 3/1996 | Fenton |
| 5,537,994 A | 7/1996 | Thornton |
| 5,566,683 A | 10/1996 | Thornton |
| 5,642,737 A | 7/1997 | Parks |
| 5,678,567 A | 10/1997 | Thornton |
| 5,755,219 A | 5/1998 | Thornton |
| 5,829,441 A | 11/1998 | Kidd et al. |
| 5,921,942 A | 7/1999 | Remmers et al. |
| 5,941,247 A | 8/1999 | Keane |
| 5,954,048 A | 9/1999 | Thornton |
| 5,983,892 A | 11/1999 | Thornton |
| 6,041,784 A | 3/2000 | Halstrom |
| 6,155,262 A | 12/2000 | Thornton |
| 6,161,542 A | 12/2000 | Halstrom |
| 6,305,376 B1 | 10/2001 | Thornton |
| 6,325,064 B1 | 12/2001 | Thornton |
| 6,374,824 B1 | 4/2002 | Thornton |
| 6,450,167 B1 | 9/2002 | David |
| 6,516,805 B1 | 2/2003 | Thornton |
| 6,729,335 B1 | 5/2004 | Halstrom |
| 6,769,910 B1 | 8/2004 | Pantino |
| 6,845,774 B2 | 1/2005 | Gaskell |
| 2003/0217753 A1 | 11/2003 | Thornton |
| 2003/0234022 A1 | 12/2003 | Belfer |
| 2005/0028827 A1 | 2/2005 | Halstrom |

FOREIGN PATENT DOCUMENTS

| | | |
|---|---|---|
| EP | 0 312 368 | 4/1989 |
| EP | 0 487 469 | 5/1992 |
| WO | 92/05752 | 4/1992 |

OTHER PUBLICATIONS

"Sleep Disorder Treatment Should be a Team Approach between Physicians and Dentists", GP, Feb. 1993, vol. 2, No. 2, pp. 17, 20-22.
PROfessional Positioners brochure, May 1984.

INTRA-ORAL APPLIANCE FOR TREATMENT OF SLEEP DISORDERS

TECHNICAL FIELD

This application relates to an intra-oral appliance for treatment of sleep disorders.

BACKGROUND

Several medical disorders appear to be related to partial or complete obstruction of an individual's pharyngeal airway during sleep. As described in the applicant's prior U.S. Pat. Nos. 5,365,945, 6,041,784 and 6,161,542, the disclosures of which are hereby incorporated by reference, snoring and obstructive sleep apnea are typically caused by complete or partial obstruction of an individual's pharyngeal airway resulting from the apposition of the rear portion of the tongue or soft palate with the posterior pharyngeal wall. Obstructive sleep apnea is a potentially lethal disorder in which breathing stops during sleep for 10 seconds or more, sometimes up to 300 times per night. Snoring occurs when the pharyngeal airway is partially obstructed, resulting in vibration of the oral tissues during respiration. These sleep disorders tend to become more severe as patients grow older, likely due to a progressive loss of muscle tone in the patient's throat and oral tissues.

Habitual snoring and sleep apnea have been associated with other potentially serious medical conditions, such as hypertension, ischemic heart disease and strokes. Accordingly, early diagnosis and treatment is recommended. One surgical approach, known as uvulopalatopharyngoplasty, involves removal of a portion of the soft palate to prevent closure of the pharyngeal airway during sleep. However, this operation is not always effective and may result in undesirable complications, such as nasal regurgitation.

A wide variety of non-surgical approaches for treating sleep disorders have also been proposed including the use of oral cavity appliances. It has been previously recognized that movement of the mandible (lower jaw) forward relative to the maxilla (upper jaw) can eliminate or reduce sleep apnea and snoring symptoms by causing the pharyngeal air passage to remain open. Several intra-oral dental appliances have been developed which the user wears at night to fix the mandible in an anterior, protruded (i.e. forward) position. Such dental appliances essentially consist of acrylic or elastomeric bite blocks, similar to orthodontic retainers or athletic mouth guards, which are custom-fitted to the user's upper and lower teeth and which may be adjusted to vary the degree of anterior protrusion.

U.S. Pat. No. 4,901,737, which issued to Toone on 20 Feb., 1990, exemplifies the prior art. Toone discloses an intra-oral appliance for reducing snoring which repositions the mandible in an inferior (open) and anterior (protrusive) position as compared to the normally closed position of the jaw. Once the dentist or physician determines the operative "snore reduction position" for a particular patient, an appropriate mold is taken of the maxillary dentition and of the mandibular dentition for formation of the appliance template. The Toone appliance includes a pair of V-shaped spacer members formed from dental acrylic which extend between the maxillary and mandibular dentition to form a unitary mouthpiece. In an alternative embodiment of the Toone invention, the spacer members are formed in two pieces and a threaded rod is provided to enable adjustment of the degree of mandibular protrusion or retrusion after the mouthpiece is formed.

European patent application No. 0,312,368 published Apr. 19, 1989 also discloses an intra-oral device for preventing snoring. This device consists of a U-shaped mouthpiece which conforms to the upper dental arch of the user and includes a sloped, lower ramp for engaging the mandibular dentition. Normal mouth motions, such as the clenching of the jaw, will cause some of the mandibular dentition to engage the underside of the ramp, thereby camming the lower jaw forward to increase the spacing between the base of the tongue and the posterior wall of the pharynx.

While prior art dental appliances have proven effective in maintaining the mandible in a protruded position to improve airway patency, they often result in undesirable side effects. One of the most common side effects is aggravation of the tempromandibular joint and related jaw muscles and ligaments, especially in individuals who have a tendency to grind their teeth during sleep. Aggravation of the tempromandibular joint has been associated with a wide variety of physical aliments, including migraine headaches. Accordingly, many individuals suffering from sleep apnea and snoring disorders are not able to tolerate existing anti-snoring dental appliances for long periods of time.

Recently it has been suggested that nocturnal teeth grinding or "bruxism" is also closely associated with partial occlusion of the pharyngeal airway during sleep. One hypothesis is that bruxism is in fact a reflex action employed by mammals to help maintain the patency of their airways. It appears that the physical clenching of the jaw which occurs during bruxism can function as an anatomical splint preventing or lessening airway occlusion. However, bruxism has several deleterious side effects, most notably gradual wear of the dental enamel. Many consumers wear mouth guards to prevent enamel wear, but such guards do not prevent or mitigate the underlying sleep disorder.

As mentioned above, the bruxing reflex can also cause problems in patients using intra-oral dental appliance configured for treatment of snoring and sleep apnea. Sleep studies suggest that bruxing individuals have a tendency to habitually move their jaws in a generally elliptical motion. This motion can cause threaded connectors coupling upper and lower dental bite blocks together to gradually loosen and eventually shear. Replacement of fractured connecting pins is inconvenient to consumers and potentially expensive to warranty providers.

The applicant's prior dental appliances for treatment of snoring and sleep apnea are designed to maintain the mandible in a preferred anterior position while also allowing a limited degree of lateral excursion of the mandible relative to the upper jaw to avoid discomfort to the tempromandibular joint and related muscles and ligaments. The applicant has also recently determined that it may also be beneficial in some patients, such as patients prone to nocturnal bruxism, to allow for a significant degree of anterior (i.e forward) excursion of mandible relative to the upper jaw in the protruded position. This allowance for anterior excursion permits habitual elliptical movement of the jaw while anatomically maintaining the patency of the pharyngeal airway. The combined effect appears to be a substantial reduction in bruxing muscular activity during sleep. Moreover, it appears that, if anterior excursion of the mandible is permitted in the protruded position, less anterior advancement of the mandible relative to the upper jaw may be necessary to achieve a reduction in snoring and apneic episodes. This in turn can reduce side effects associated with long-term wear of anti-snoring dental appliances, such as bite displacement and misalignment.

SUMMARY OF INVENTION

In accordance with the invention, a dental appliance is provided comprising an upper member conforming to the patient's maxillary dentition; a lower member conforming to the patient's mandibular dentition; and a connecting assembly for adjustably coupling the upper and lower members together. The connecting assembly includes a first element mounted on the upper member, the first element having a cavity therein; a second element mounted on the lower member; and a connector having a first end captured within the cavity and a second end adjustably connectable to the second element. The connecting assembly maintains the lower member in a protruded position relative to the upper member to maintain the patency of the user's pharnygeal airway while permitting anterior and lateral movement of the lower member relative to the upper member in the protruded position.

In one embodiment, the first element of the dental appliance may include a first plate mounted on the upper member and a second plate releasably connectable to the first plate, wherein the first and second plates together define the cavity. The connector may include an enlarged head formed at the first end of the connector and a shaft extending downwardly from the head. The second end of the connector remote from the shaft may be selectively connectable to the second element at one of a plurality of spaced-apart positions.

The cavity may include a rear wall which is adjustable in position for constraining rearward movement of the connector head and hence relative rearward movement of the lower member relative to the upper member. For example, in one embodiment, the first element comprises a slot in a rear portion thereof and an adjustment bar which is optionally insertable into the slot to adjust the position of the rear wall of said cavity. The adjustment bar may include a first flat side and a second recessed side, wherein the adjustment bar is optionally insertable into the slot in different orientations to vary the position of the rear wall.

The invention also encompasses methods for treating sleep disorders, such as snoring, sleep apnea and nocturnal bruxism, by making and using the intra-oral appliance described herein.

BRIEF DESCRIPTION OF DRAWINGS

In drawings which describe embodiments of the invention but which should not be construed as restricting the spirit or scope thereof.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
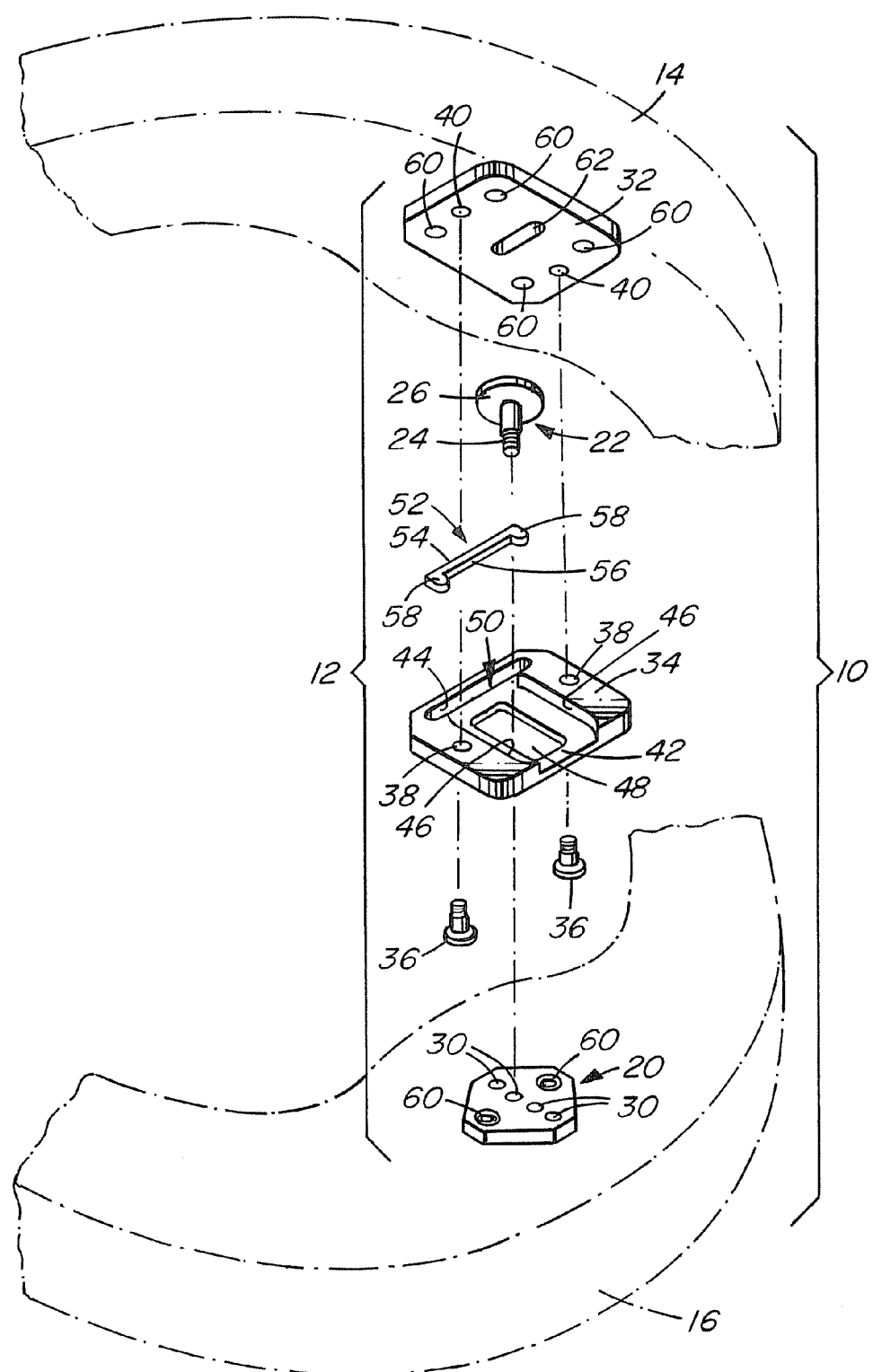
FIG. 1 is an exploded, isometric view of the applicant's connecting assembly for connecting together upper and lower bite blocks shown in dotted outline.

This application relates to a dental appliance 10 for maintaining the patency of a user's pharyngeal airway. Appliance 10 can be used for treating or preventing a variety of disorders associated with airway obstruction, including snoring, sleep apnea and nocturnal bruxism. As shown in FIG. 1, appliance 10 comprises a connecting assembly 12 for adjustably coupling an upper bite block or member 14 and a lower bite block or member 16 together. As explained in the applicant's U.S. Pat. Nos. 5,365,945, 6,041,784 and 6,161,542, which are hereby incorporated by reference, connecting assembly 12 is configured so that lower bite block 16 is maintained in an anteriorly protruded (i.e. forward) position relative to upper bite block 14 while still permitting some relative movement of bite blocks 14, 16 in the protruded position.

As shown best in FIGS. 2(a)-2(c) and 4(a)-4(b), connecting assembly 12 includes a first connecting element 18 secured to upper bite block 14 and a second connecting element 20 secured to lower bite block 16. Connecting elements 18, 20 are adjustably coupled together by a stylus connector 22 having a shaft 24 and an enlarged head 26. Stylus head 26 is captured within a cavity 28 formed within connecting element 18. As shown in the drawings, stylus shaft 18 extends downwardly and may be threadedly coupled to a selected one of a series of internally threaded apertures 30 spaced apart on second connecting element 20. As described further below, since stylus 22 is capable of moving to a limited extent within cavity 28, this enables lower bite block 16 to move relative to upper bite block 14 when appliance 10 is worn by a user.

In the illustrated embodiment, first connecting element 18 comprises a first plate 32 and a second plate 34 which may be releasably coupled together. For example, as best shown in FIG. 1, screw fasteners 36 may be passed through apertures 38 formed in second plate 34 and coupled to internally threaded apertures 40 formed in first plate 32. As will be apparent to a person skilled in the art, many other means for fastening plates 32, 34 together may be envisaged. For example, apertures 38 may also be internally threaded for receiving fasteners 36.

Figure 3A:
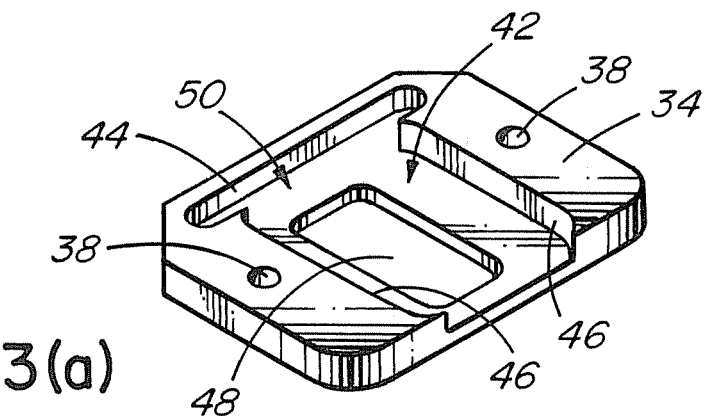
FIG. 3(a) is an isometric view of a second plate portion of the connecting assembly with the adjustment bar removed.
Figure 3B:
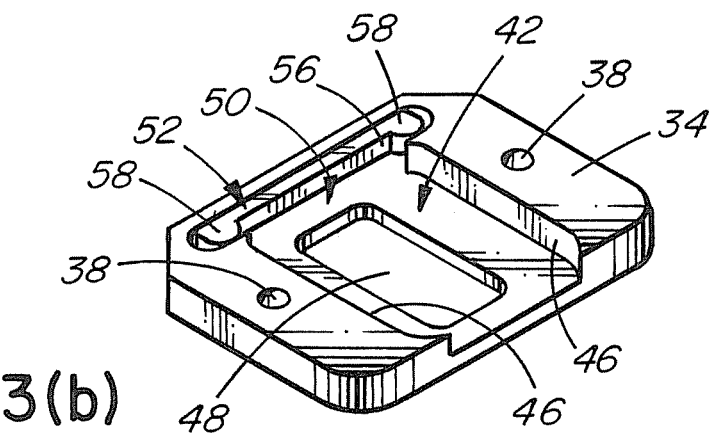
FIG. 3(b) is an isometric view of a second plate portion of the connecting assembly with the adjustment bar inserted in a first orientation.
Figure 3C:
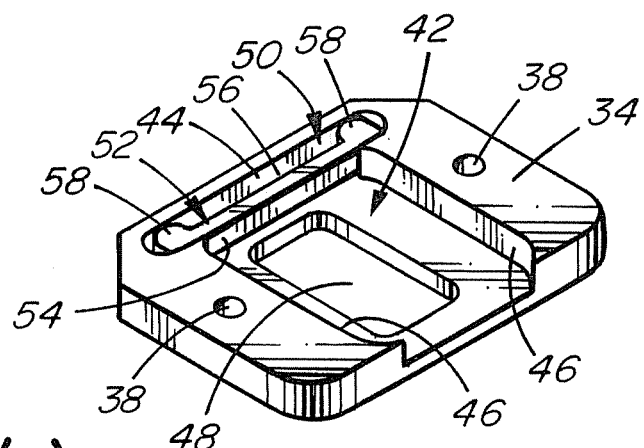
FIG. 3(c) is an isometric view of a second plate portion of the connecting assembly with the adjustment bar inserted in a second orientation.
Figure 4A:
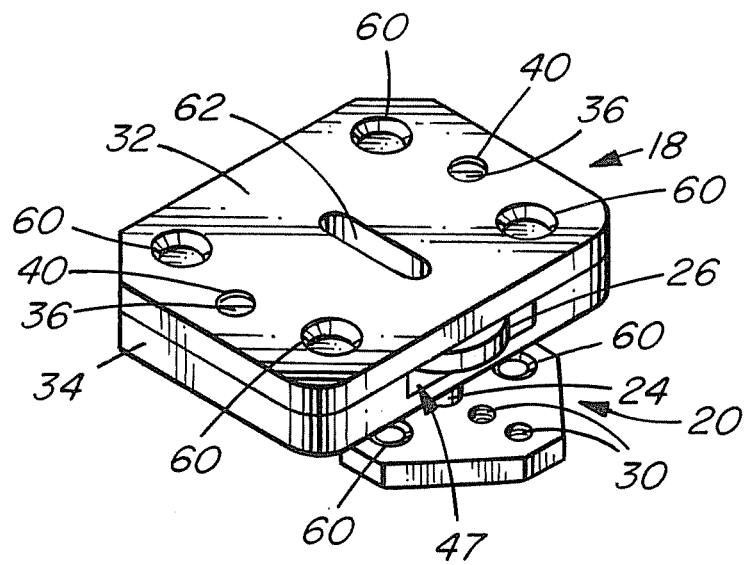
FIG. 4(a) is an assembled, isometric view of the connecting assembly showing the lower, second connecting element in a forwardmost position relative to the upper, first connecting element.
Figure 4B:
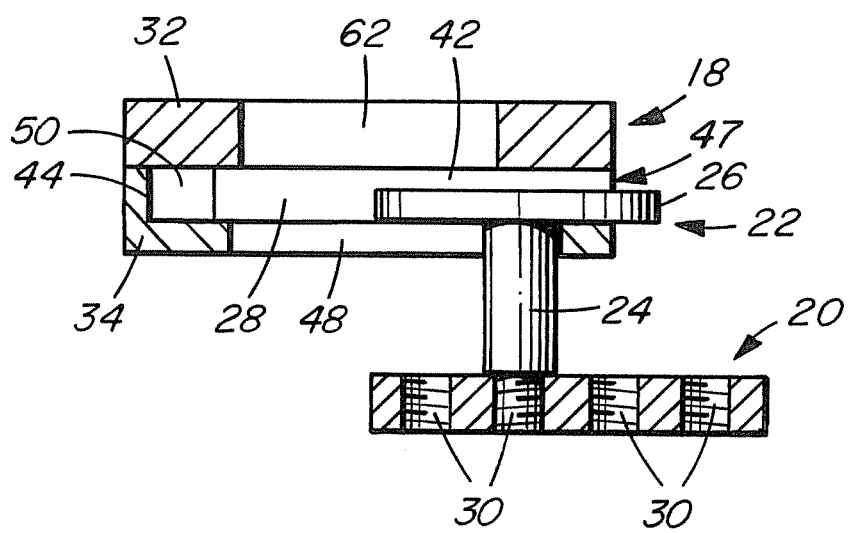
FIG. 4(b) is a cross-sectional view of the assembly of FIG. 4(a).

As best shown in FIGS. 3(a)-3(c), second plate 34 includes a slot 42 defined by a rear wall 44 and opposed side walls 46. A cut-out 47 is provided at the front end of slot 42 (FIGS. 4(a) and 4(b). An opening 48 is formed in a central, bottom portion of slot 42. When connecting plates 32 and 34 are coupled together, slot 42 defines the metes and bounds of cavity 28 formed in connecting element 18 for capturing stylus head 26. In its forwardmost position (i.e. when stylus shaft 24 bears against the forward edge of aperture 48), a portion of stylus head 26 may project through cut-out 47 (FIG. 4(a)).

As shown best in FIGS. 1 and 2(a)-2(c)), slot 42 has an elongated, trans-versely extending rear portion 50 for removably receiving an adjustment bar 52. Bar 52 includes an elongated segment having a flat surface 54 on one side thereof and a recessed surface 56 formed on the other side thereof As shown best in FIG. 1, recessed surface 56 is located between two enlarged feet 58 located at end portions of bar 52. Feet 58 have a width approximating the width of slot rear portion 50 so that adjustment bar 52 fits snugly therein.

As shown best in FIGS. 3(a)-3(c)), adjustment bar 52 may be optionally placed in slot rear portion 50 in different orientations to vary the size of slot 42 and hence the size of cavity 28. FIG. 3(a) shows slot 42 with adjustment bar 52 removed entirely. FIG. 3(b) shows adjustment bar 52 placed in slot rear portion 50 with flat surface 54 bearing against rear wall 44 and recessed surface 56 facing the interior of slot 42. FIG. 3(c) shows adjustment bar 52 placed in slot rear portion 50 with flat surface 54 facing the interior of slot 42 and feet 58 bearing against rear wall 44.

Figure 2A:
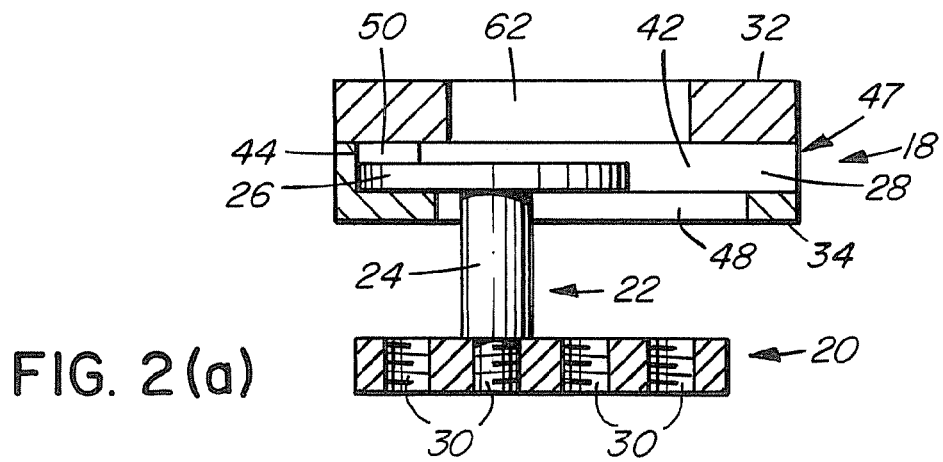
FIG. 2(a) is an assembled, cross-sectional view of the connecting assembly with an adjustment bar removed.

As mentioned above, adjustment bar 52 provides a convenient means for varying the effective size of slot 42 and hence the size of cavity 28. As shown in FIG. 2(a), when adjustment bar 52 is removed, rearward movement of stylus 22, and hence connecting element 20, relative to connecting element 18 is not constrained until a rear edge of stylus head 26 contacts the rear wall 44 of slot 42. When adjustment bar 52 is inserted in the orientation shown in FIGS. 2(b) and 3(b), the effective rear boundary of slot 42 is advanced forwardly by the width of the elongated segment of bar 52 (in this example, approximately one millimeter). When adjustment bar is inserted in the orientation shown in FIGS. 2(c) and 3(c), the effective rear boundary of slot 42 is advanced forwardly by a further increment corresponding to the full width of adjustment bar feet 58 (in this example, approximately two millimeters in total). Adjustment bar 58 therefore enables very fine incremental adjustment of the effective size of slot 42 and hence the relative position of connecting elements 18, 20.

In use, dental appliance 20 is custom-fitted to suit the requirements of each individual patient. Usually the first step in the fitting procedure is for the dentist or physician to assess the natural range of motion of the patient's jaw and the likely degree of pharyngeal occlusion. This may be determined by physical examinations, sleep studies, x-rays and the like. For example, the dentist, physician or other clinician may create a gothic arch tracing representative of the natural range of motion of a patient's mandible as described in Applicant's U.S. Pat. No. 5,722,828 dated Mar. 3, 1998, which is hereby incorporated by reference. The tracing is used in the fabrication of a dental bite registration mold for the patient. The mold may in turn be used to mount casts of the patient's dentition in a specific relationship as required for prosthetic or therapeutic purposes.

More particularly, molds of the patient's existing maxillary and mandibular dentition may be prepared to enable casting of bite blocks 14 and 16. Bite blocks 14, 16 are typically formed of a heat-curable elastomeric and/or acrylic material as is well-known in the art. Connecting assembly 12 is then secured to bite blocks 14, 16 to releasably couple them together in the preferred relative relationship as shown in FIG. 1. First plate 32 of connecting element 18 is secured to upper bite block 14 and connecting element 20 is secured to lower bite block 16. Both plate 32 and connecting element 20 include retention apertures 60 to allow the soft elastomeric dental acrylic to flow therein to ensure a strong bond. Second plate 34 of connecting element 18 is then secured to first plate 32 as described above with the head 26 of stylus 22 captured within internal cavity 28. Depending upon the specific amount of anterior protrusion desired, adjustment bar 52 may be optionally inserted within slot rear portion 50 in either of the orientations shown in the drawings and described above.

Figure 2B:
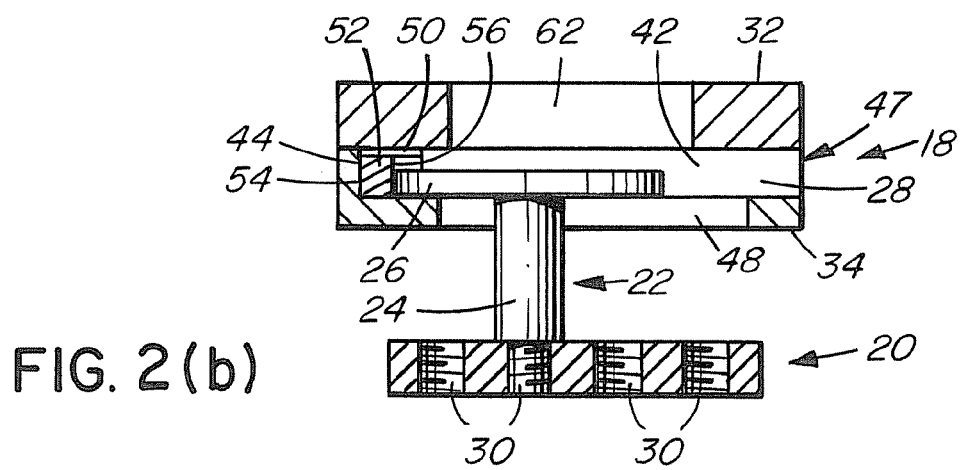
FIG. 2(b) is an assembled, cross-sectional view of the connecting assembly with an adjustment bar inserted in a first orientation
Figure 2C:
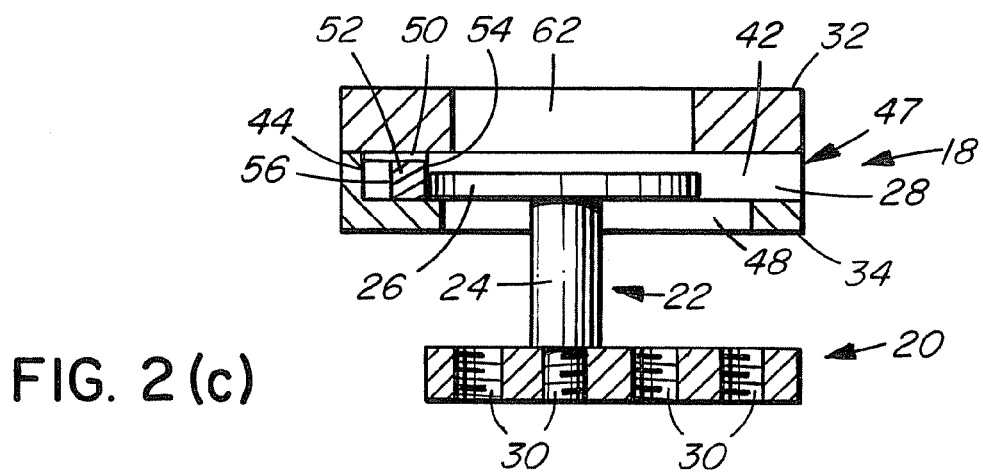
FIG. 2(c) is an assembled, cross-sectional view of the connecting assembly with the adjustment bar inserted in a second orientation.

Once connecting element 18 is assembled, the shaft 24 of stylus 22 extends downwardly through slot aperture 48. The threaded end of stylus shaft 22 may then be connected to one of the internally threaded apertures 30 formed on connecting element 20. Plate 32 may include an access slot or aperture 62 to enable insertion of a small wrench or other tool into cavity 28 to engage the head 26 of stylus 22 for turning purposes. In one embodiment of the invention, apertures 30 may be spaced approximately 2 millimeters apart. As indicated above, the specific aperture 30 selected will depend upon the anatomy of the patient and the nature of his or her sleep disorders. Ordinarily the minimum degree of anterior protrusion of the mandible relative to the upper jaw that will alleviate snoring, sleep apnea and/or bruxism symptoms is initially selected. If necessary, further incremental forward advancement of the mandible may be achieved, either by insertion of adjustment bar 52 into rear slot portion 50 in one of the two available orientations as discussed above, or by connecting stylus 22 to a more forward aperture 30 on connecting element 20. As indicated above, once the desired setting has been selected, rearward movement of stylus 22 and hence connecting element 20 and bottom bite block 16 is constrained when stylus head 26 contacts the rear boundary of slot 42 (i.e. the rear wall of cavity 28 as shown in FIGS. 2(a)-2(c)).

An important feature of the present invention is that when connecting assembly 12 and hence bite blocks 14, 16 are configured in the preferred relative spacial relationship, assembly 12 permits both lateral and anterior (forward) excursion of lower bite block 16 (i.e. the patient's mandible) relative to upper bite block 14 (i.e. the patient's upper jaw). That is, stylus head 26 may travel within cavity 28 to the forwardmost position shown in FIGS. 4(a) and 4(b) and laterally between slot side walls 46. In one embodiment of the invention, connecting assembly 12 may permit a maximum of between 4-6 millimeters of anterior slide depending upon the specific setting selected. This permits elliptical motion of the patient's mandible in the protruded position, which may be a habitual reflex in patients prone to bruxism. The applicant has determined that allowing such anterior motion, while maintaining the mandible in an anteriorly protruded position to maintain airway patency, significantly reduce bruxing symptoms and avoids potentially harmful muscular activity during sleep. In some patients, if anterior excursion of the mandible is permitted in the protruded position as may be accomplished by applicant's invention, less anterior advancement of the mandible relative to the upper jaw may be necessary to achieve a reduction in snoring and apneic episodes. This in turn can reduce side effects associated with long-term wear of anti-snoring dental appliances, such as bite displacement and misalignment.

As will be apparent to those skilled in the art in the light of the foregoing disclosure, many alterations and modifications are possible in the practice of this invention without departing from the spirit or scope thereof. For example, in an alternative embodiment of the invention bite blocks 14, 16 may be cast by the user in a manner similar to readily available over-the-counter sports mouth guards rather than custom-fitted by a dentist, physician or other clinician. Many other variations and alternatives are possible. Accordingly, the scope of the invention is to be construed in accordance with the substance defined by the following claims.

What is claimed is:

1. A dental appliance comprising:
   (a) an upper member conforming to a user's maxillary dentition;
   (b) a lower member conforming to a user's mandibular dentition; and
   (c) a connecting assembly for coupling said upper and lower members together, wherein said connecting assembly comprises:

(i) a first element mounted on said upper member, wherein said first element comprises a cavity defined within an interior of said first element, and wherein a lower surface of said first element has an aperture formed therein in communication with said cavity;

(ii) a second element mounted on said lower member; and (iii) a connector having a first end having a size smaller than a size of said cavity such that said first end is loosely captured within said cavity, a second end adjustably connectable to said second element to precisely fix the vertical distance between said upper and lower members, and a shaft extending through said aperture between said first end and said second end, wherein said first end is freely movable relative to said upper member within said cavity when said dental appliance is worn during sleep by a user, wherein said connecting assembly:

(1) maintains said lower member in an anteriorly protruded position relative to said upper member; and (2) permits anterior, posterior, and lateral excursion of said lower member relative to said upper member in said protruded position to accommodate a bruxing reflex of a user, wherein said aperture has a spacing between a rear edge and a front edge thereof which is substantially larger than the diameter of said shaft.

2. The dental appliance as defined in claim 1, wherein said first element comprises:

(a) a first plate mounted on said upper member; and (b) a second plate releasably connectable to said first plate, wherein said first and second plates together define said cavity.

3. The dental appliance as defined in claim 2, wherein said first element further comprises a slot located between said first and second plates to permit at least part of said connector to protrude anteriorly from said cavity.

4. The dental appliance as defined in claim 1, wherein said connector comprises a head formed at said first end of said connector and wherein said shaft extends downwardly from said head, wherein said second end of said connector is an end portion of said shaft remote from said head.

5. The dental appliance as defined in claim 4, wherein said second end of said connector is selectively connectable to said second element at one of a plurality of spaced-apart positions.

6. The dental appliance as defined in claim 5, wherein said second end of said connector is threadedly connectable to said second element.

7. The dental appliance as defined in claim 1, wherein said first element comprises a slot in a rear portion thereof, wherein said first element comprises an adjustment bar which is optionally insertable into said slot to adjust the position of a rear wall of said cavity.

8. The dental appliance as defined in claim 7, wherein said adjustment bar has a first flat side and a second recessed side, wherein said adjustment bar is optionally insertable into said slot in different orientations to vary the position of said rear wall.

9. The dental appliance as defined in claim 1, wherein said connecting assembly permits up to 4 mm of anterior excursion of said lower member relative to said upper member in said protruded position.

10. The dental appliance as defined in claim 1, wherein said connecting assembly permits up to 6 mm of anterior excursion of said lower member relative to said upper member in said protruded position.

11. The dental appliance as defined in claim 1, wherein posterior movement of said lower member relative to said upper member is constrained in said protruded position when said first end of said connector contacts a rear wall of said cavity.

12. The dental appliance as defined in claim 1, wherein said cavity has a rear wall which is adjustable in position.

13. The dental appliance as defined in claim 1, wherein said aperture is in the shape of a rectangle and wherein said spacing between said rear edge and said front edge is the length of said rectangle.

14. The dental appliance as defined in claim 13, wherein said aperture has a width at least twice as large as said diameter of said shaft.

15. The dental appliance as defined in claim 14, wherein said aperture has a width approximately three times larger than said diameter of said shaft.

16. The dental appliance as defined in claim 1, wherein said spacing is at least 4 times larger than the diameter of said shaft.

17. The dental appliance as defined in claim 16, wherein said spacing is at least 5 times larger than the diameter of said shaft.

18. The dental appliance as defined in claim 1, wherein said aperture has a lateral spacing between side edges thereof which is substantially larger than said diameter of said shaft.

19. A connecting assembly for use in a dental appliance having an upper member conforming to the user's maxillary dentition and a lower member conforming to the user's mandibular dentition, said connecting assembly comprising:

(a) a first element mountable on said upper member, wherein said first element comprises a cavity defined within an interior of said first element, and wherein said first element has an aperture formed therein in communication with said cavity;

(b) a second element mountable on said lower member; and (c) a connector having a first end having a size smaller than a size of said cavity such that said first end is loosely captured within said cavity, a second end adjustably connectable to said second element to precisely fix the vertical distance between said upper and lower members, and a shaft extendable through said aperture between said first end and said second end, wherein said first end is freely movable relative to said upper member within said cavity when said dental appliance is worn during sleep by a user, wherein said connecting assembly:

(1) maintains said lower member in an anteriorly protruded position relative to said upper member; and (2) permits anterior, posterior, and lateral excursion of said lower member relative to said upper member in said protruded position to accommodate a bruxing reflex of a user, wherein said aperture has a spacing between a rear edge and a front edge thereof which is substantially larger than the diameter of said shaft.

20. The connecting assembly as defined in claim 19, wherein said assembly comprises:

(a) a first plate mountable on said upper member; and (b) a second plate releasably connectable to said first plate, wherein said first and second plates together define said cavity.

21. The connecting assembly as defined in claim 20, wherein said connector comprises a head formed at said first end of said connector and wherein said shaft extends downwardly from said head, wherein said second end of said connector is an end portion of said shaft remote from said head.

22. The connecting assembly as defined in claim 21, wherein said second end of said connector is selectively connectable to said second element at one of a plurality of spaced-apart positions.

23. The connecting assembly as defined in claim 22, wherein said second end of said connector is threadedly connectable to said second element.

24. The connecting assembly as defined in claim 20, wherein said first element further comprises a slot located between said first and second plates to permit at least part of said connector to protrude anteriorly from said cavity.

25. The connecting assembly as defined in claim 19, wherein said first element comprises a slot in a rear portion thereof, wherein said first element comprises an adjustment bar which is optionally insertable into said slot to adjust the position of a rear wall of said cavity.

26. The connecting assembly as defined in claim 25, wherein said adjustment bar has a first flat side and a second recessed side, wherein said adjustment bar is optionally insertable into said slot in different orientations to vary the position of said rear wall.

27. The connecting assembly as defined in claim 19, wherein said connecting assembly permits up to 4 mm of anterior excursion of said second element relative to said first element.

28. The connecting assembly as defined in claim 19, wherein said connecting assembly permits up to 6 mm of anterior excursion of said second element relative to said first element.

29. The connecting assembly as defined in claim 19, wherein posterior movement of said lower member relative to said upper member is constrained in said protruded position when said first end of said connector contacts a rear wall of said cavity.

30. A method of treating a sleep disorder by adjustably maintaining a patient's mandible in an anteriorly protruded position, comprising:
(a) casting an upper bite block by taking a mold of the patient's maxillary dentition;
(b) casting a lower bite block by taking a mold of the patient's mandibular dentition;
(c) securing a first connecting element to an undersurface of said upper bite block in an anterior region thereof, said first connecting element comprising a cavity defined within an interior thereof and a connector having an upper end having a size smaller than a size of said cavity such that said upper end is loosely captured in said cavity and is freely movable within said cavity when said dental appliance is worn during sleep by a user, said first element having a lower surface having an aperture formed therein in communication with said cavity said connector further comprising a downwardly extending shaft extending through said aperture and a lower end on said shaft remote from said upper end;
(d) securing a second element to an upper surface of said lower bite block in an anterior region thereof;
(e) determining a preferred protruded position of said mandible required to alleviate the patient's sleep disorder; and
(f) releasably securing said lower end of said connector to said second element at a fixed position corresponding to said preferred protruded position as determined in step (e), wherein said connecting element permits anterior, posterior, and lateral excursion of said lower member relative to said upper member in said protruded position to accommodate a bruxing reflex of a user, wherein said aperture has a spacing between a rear edge and a front edge thereof which is substantially larger than the diameter of said shaft.

31. The method as defined in claim 30, wherein said sleep disorder is selected from the group consisting of snoring, sleep apnea and nocturnal bruxism.

32. The method as defined in claim 31, wherein said sleep disorder is nocturnal bruxism.

33. A dental appliance comprising:
(a) an upper member conforming to a user's maxillary dentition;
(b) a lower member conforming to a user's mandibular dentition; and
(c) a connecting assembly for coupling said upper and lower members together, wherein said connecting assembly comprises:
(i) a first element mounted on said upper member, wherein said first element comprises a cavity defined within an interior of said first element, and wherein a lower surface of said first element has an aperture formed therein in communication with said cavity;
(ii) a second element mounted on said lower member; and
(iii) a connector having a first end having a size smaller than a size of said cavity such that said first end is loosely captured within said cavity, a second end adjustably connectable to said second element to precisely fix the vertical distance between said upper and lower members, and a shaft extending through said aperture between said first end and said second end, wherein said first end is freely movable relative to said upper member within said cavity when said dental appliance is worn during sleep by a user,
wherein said connecting assembly:
(1) maintains said lower member in an anteriorly protruded position relative to said upper member; and
(2) permits a sufficient degree of multi-directional free movement of the user's mandible in said protruded position to accommodate a bruxing reflex of the user, wherein said aperture has a spacing between a rear edge and a front edge thereof which is substantially larger than the diameter of said shaft.

34. A connecting assembly for use in a dental appliance having an upper member conforming to the user's maxillary dentition and a lower member conforming to the user's mandibular dentition, said connecting assembly comprising:
(a) a first element mountable on said upper member, wherein said first element comprises a cavity defined within an interior of said first element, and wherein a lower surface of said first element has an aperture formed therein in communication with said cavity;
(b) a second element mountable on said lower member; and
(c) a connector having a first end having a size smaller than a size of said cavity such that said first end is loosely captured within said cavity, a second end adjustably connectable to said second element to precisely fix the vertical distance between said upper and lower members, and a shaft extending through said aperture between said first end and said second end, wherein said first end is freely movable relative to said upper member within said cavity when said dental appliance is worn during sleep by a user,
wherein said connecting assembly:
(1) maintains said lower member in an anteriorly protruded position relative to said upper member; and
(2) permits a sufficient degree of multi-directional free movement of the user's mandible in said protruded position to accommodate a bruxing reflex of the user, wherein said aperture has a spacing between a rear edge and a front edge thereof which is substantially larger than the diameter of said shaft.

* * * * *